United States Patent [19]

Oliver et al.

[11] Patent Number: 5,359,879
[45] Date of Patent: Nov. 1, 1994

[54] SCANNING MICRO-SCLEROMETER

[75] Inventors: Warren C. Oliver, Knoxville; Peter J. Blau, Oak Ridge, both of Tenn.

[73] Assignee: Martin Marietta Energy Systems, Inc., Oak Ridge, Tenn.

[21] Appl. No.: 971,175

[22] Filed: Nov. 4, 1992

[51] Int. Cl.$^5$ .......................... G01N 3/46; G01N 3/56
[52] U.S. Cl. ................................. 73/7; 73/81; 73/573
[58] Field of Search ............. 73/7, 8, 78, 81, 573, 73/579

[56] References Cited

U.S. PATENT DOCUMENTS

| | | | |
|---|---|---|---|
| 2,338,537 | 1/1944 | Podesta | 73/7 |
| 2,488,689 | 11/1949 | Keenan et al. | 73/81 X |
| 2,913,899 | 11/1959 | Wohler | 73/81 X |
| 2,950,617 | 8/1960 | Campbell | 73/7 |
| 3,955,404 | 5/1976 | Bickel et al. | 73/579 X |
| 4,382,253 | 5/1983 | Belthle | 340/680 |
| 4,472,961 | 9/1984 | Rehfeld et al. | 73/7 |
| 4,791,807 | 12/1988 | Oechsle | 73/78 |
| 4,848,141 | 7/1989 | Oliver et al. | 73/81 |
| 4,899,594 | 2/1990 | Wolfer et al. | 73/104 X |
| 4,958,511 | 9/1990 | Marcus | 73/7 |
| 5,092,163 | 3/1992 | Young | 73/105 |
| 5,281,535 | 1/1994 | Wei et al. | 73/9 X |

FOREIGN PATENT DOCUMENTS

| | | | |
|---|---|---|---|
| 1249664 | 1/1989 | Canada | 73/579 |
| 2595824 | 9/1987 | France | 73/78 |
| 214735 | 8/1989 | Japan | 73/7 |
| 136080 | 4/1961 | U.S.S.R. | 73/7 |
| 352189 | 1/1973 | U.S.S.R. | 73/81 |
| 1619132 | 1/1991 | U.S.S.R. | 73/78 |

OTHER PUBLICATIONS

*Industrial Lab.* (*USA*) vol. 46, No. 5 May 1980, pp. 508–512; "Microhardness Tester with Automatic Recording of Indentation or Scratching Diagram"; V. F. Berdikou et al.; in 73/81.

*Patent Abstracts of Japan*; ABS Grp. No. p. 776 vol. 12, No. 1, ABS pub. date Oct. 25, 1988 (63–140939).

ABS Grp. No. p. 964, vol. 13, No. 524, ABS pub. date Nov. 22, 1989 (01–214735).

ABS Grp No. p. 967, vol. 13, No. 533, ABS Pub. date Nov. 28, 1989 (01–219539).

*Primary Examiner*—Tom Noland
*Attorney, Agent, or Firm*—Edward A. Pennington; George L. Craig; James M. Spicer

[57] ABSTRACT

A scanning micro-sclerometer measures changes in contact stiffness and correlates these changes to characteristics of a scratch. A known force is applied to a contact junction between two bodies and a technique employing an oscillating force is used to generate the contact stiffness between the two bodies. As the two bodies slide relative to each other, the contact stiffness changes. The change is measured to characterize the scratch.

3 Claims, 2 Drawing Sheets

SCANNING MICRO-SCLEROMETER

This invention was made with Government support under contract DE-AC05-84OR21400 awarded by the U.S. Department of Energy to Martin Marietta Energy Systems, Inc. and the Government has certain rights in this invention.

FIELD OF THE INVENTION

The present invention relates generally to measuring and testing and, more specifically, to a micro-sclerometer capable of measuring scratch characteristics during sliding contact between two objects. The present invention uses measured contact stiffness to characterize a scratch while it is being produced during nano-scale machining processes.

BACKGROUND OF THE INVENTION

Whenever two bodies with arbitrary properties are brought into sliding contact, control of the size and mechanical properties of the contact is normally achieved by controlling the force or interference between the bodies. These two techniques become difficult or impossible to use as the size of the contact is reduced. For instance, if a contact of very small dimensions is required, the physical interference between the two becomes so small as to be nearly impossible to measure, particularly as the two bodies move relative to one another. Because the forces involved in establishing such small contacts are themselves extremely small, they are also difficult to measure and control. This is particularly true because as the two bodies move, the physical interference will change as just described. Thus, it is difficult to control very small sliding contact as those that would be used in nano-scale machining, nanoprofilometry, atomic force microscopy images and very low load friction measurements.

U.S. Pat. No. 4,848,141 to Oliver et al. describes a method for continuously measuring the stiffness and area of contact between two bodies, in which elastic stiffness of a junction is measured by introducing a relatively small oscillatory mechanical force at a known frequency to the junction and measuring the subsequent displacement response using AC signal-handling techniques. The apparatus provides a continuous measurement proportional to the stiffness and the area of contact between the bodies.

The aforementioned U.S. Pat. describes an adequate technique for characterizing a point depression as it is produced in a surface using contact stiffness, but does not describe characterizing a scratch. Scratch characteristics are important parameters in the field of nano-scale machining. Prior art techniques using force and size measurements are deficient. These are typically inadequate because the magnitude of the forces and distances involved are exceedingly small, to the point of being unmeasurable and thus unsuitable for control purposes. Thus, a continuing need exists for improved apparatuses and methods for the continuous measurement of scratch characteristics during sliding contact between two bodies.

SUMMARY OF THE INVENTION

An object of the present invention is to provide an apparatus and method for continuously measuring scratch characteristics during sliding contact between two bodies which permits the dimensions of the contact area to be measured during sliding contact.

Another object of the present invention is to provide an apparatus and method for continuously measuring scratch characteristics during sliding contact between two bodies capable of measuring scratch characteristics for extremely small contact areas.

Still another object of the present invention is to provide an apparatus and method for continuously measuring scratch characteristics during sliding contact between two bodies in which the contact area can be controlled during nano-scale machining or other processes by using the measurement of elastic stiffness as a control parameters.

These and other objects of the invention are met by providing a method for continuously measuring scratch characteristics during sliding contact between first and second bodies, comprising the steps of applying an oscillating mechanical excitation at an arbitrary selected fixed frequency and a known amplitude to the contact junction of the first and second bodies and simultaneously applying a load independently of the fixed frequency to the contact junction, measuring the resulting mechanical response between the first and second bodies relative to the applied oscillatory excitation at the load as an indication of the stiffness of contact between the first and second bodies, imparting sliding contact between the first and second bodies by moving one relative to the other, and measuring changes in the measured stiffness over time while maintaining the load on the contact junction, the change in stiffness being indicative of scratch characteristics.

In effect, the apparatus and method of the present invention characterizes the contact through its elastic stiffness via a special oscillating technique. The elastic stiffness is related to the elastic moduli of the two bodies and the square root of the contact area between them. This relationship is such that a measurement of the elastic stiffness is extremely sensitive at very small contacts. For instance, using this technique it is possible to accurately control the width of a scratch on metal even when the width of the scratch is only 0.01 $\mu$m or less.

This capability will allow mechanical, nano-scale machining to compete with the most sophisticated mask generation techniques now available in the semiconducting industry.

Other objects, advantages and salient features of the invention will become apparent from the following detailed description, which taken in conjunction with the annexed drawings, discloses preferred embodiments of the invention.

DETAILED DESCRIPTION OF THE INVENTION

Figure 1:
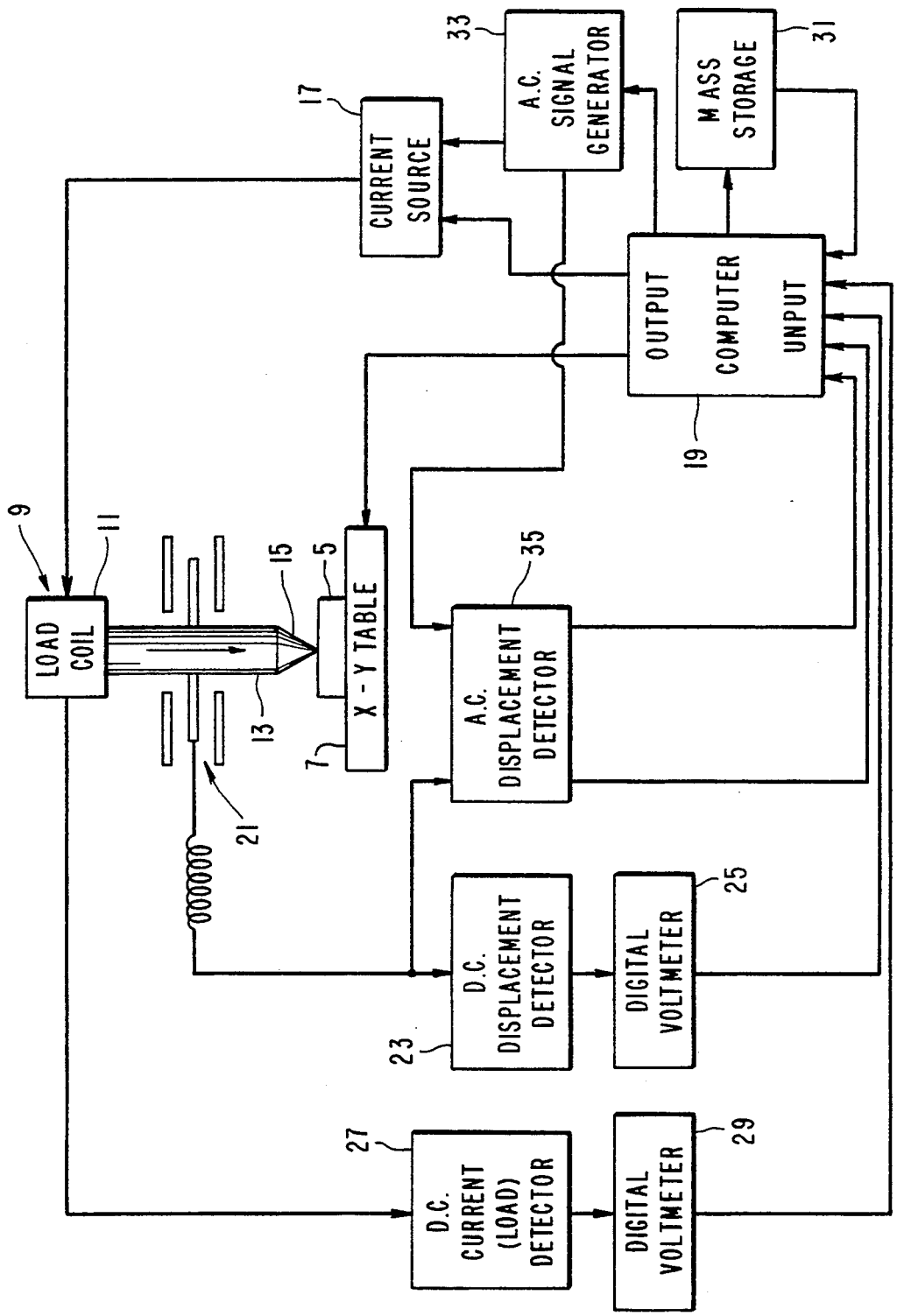
FIG. 1 is a schematic diagram of a commercially available indentation testing system modified to carry out the method of continuously measuring scratch characteristics during sliding contact between two bodies according to the present invention.

Referring to FIG. 1, there is shown a schematic diagram of an indentation system, such as a Nanoindenter system sold by NANO Instruments, Inc. of Knoxville, Tenn. This system is substantially the same as that which is illustrated in the aforementioned U.S. Pat. No. 4,848,141 which is incorporated herein by reference. The apparatus described therein was modified for testing a sample of material 5. The sample 5 is placed at a known location on a computer controlled X-Y table 7 with the surface to be tested facing up. An electromagnetically driven indenter arrangement 9 is positioned over the sample 5 and includes a current driven load coil 11 activated by the application of electrical current from a computer controlled variable current source 17 to move the prove tip 15 downward into engagement with the sample 5. Once the tip contacts the sample a preselected force pattern is applied to the indenter by the programmed variation of the current applied to the drive coil 11. The probe tip 15 may be in the form of a typical triangular pyramidal diamond probe with an end radius of about 500 Angstroms.

The current source 17 is controlled by the system computer 19' which also controls the X-Y table 7. The displacement of the probe 13 is measured by a capacitive displacement gage 21, whose output is connected to a DC displacement detector 23. The detector 23 digitizes the DC displacement signal which is fed through a digital voltmeter 25 to an input of the computer 19'. The voltmeter 25 provides a calibrated readout of the probe displacement to an operator during testing procedures.

The force applied to the sample through the indenter probe 13 is monitored by a DC current detector 27 which senses the DC drive current applied to the load coil 11. The DC load current is digitized by the detector 27 and fed through a second digital voltmeter 29 to a further input of computer 19'. The computer may be connected to a mass storage device 31 in which data and system operating parameters are stored.

Using the system as described above, a sample 5 is positioned at a known location on the X-Y table 7 and the programmed computer 19 is signaled to start the test procedure. The computer is programmed to perform a prescribed indentation test, single or multiple indentations at designated locations on the sample, automatically. The probe is lowered at a very slow rate until contact is made with the sample. Then the computer applies a programmed increasing DC current from source 17 to the load coil 11 of the indenter which forces the indenter against the sample 5 until a preselected junction loading or displacement level is reached and then the force is removed at the same rate to unload the junction. During this loading and unloading cycle, the computer records the junction loading taken from the DC current (load) detector 27 and the probe displacement taken from the DC displacement detector 23. These values may be stored in the mass storage unit 31 for subsequent use in determining the various mechanical properties of the sample as outlined above.

In accordance with the method of the aforementioned U.S. Pat. No. 4,848,141, to continuously measure the stiffness of the contact between two bodies such as the indenter probe tip 15 and the sample 5 during the loading and unloading cycle, the Nanoindenter system is modified to include a means for applying a small mechanical vibrational force to the junction of the indenter probe and the sample and monitoring the resulting displacement relative to the applied force as a measure of the stiffness between the two bodies. The force may be applied in the form of an oscillatory force (AC force), typically about $10^{-8}$N (Newton), by superimposing an AC current onto the DC drive current applied to the drive coil 11. The frequency of the AC force applied is typically in the range of from 0.5 to 200 Hz for the system depicted in FIG. 1; however, depending on the design of the probe mounting assembly involved, the concept can work from about 0.5 Hz to 1 MHz. The amplitude of the oscillating force may be in the range of from about $10^{-10}$ to 1N, depending on the area of the contact.

This procedure may be accomplished by adding an AC signal generator 33 under control of the computer 19' to inject an AC signal into the output current signal of the current source 17 and detecting the resulting AC displacement by means of an AC displacement detector 35. The detector 35 may be a lock-in amplifier which is tuned to measure the amplitude of the AC displacement at the applied frequency together with the phase of the displacement signal relative to the applied signal. The amplitude and phase signals are digitized by the detector 35 and fed to separate inputs of the computer 19' for analysis or storage along with the DC force and displacement information during a loading and unloading cycle.

Using the AC force (F), phase ($\Phi$) and AC displacement h($\omega$) information, the stiffness (S) may be determined continuously in accordance with the following relationship:

$$\tan(\Phi) = \omega c/[S + k - m\omega^2]$$

where:
 $\omega$ = frequency of applied AC force component;
 c = damping coefficient of the probe mounting assembly;
 k = probe mounting assembly spring constant; and
 m = probe and assembly mass.

The probe assembly of the Nanoindenter system is supported by leaf springs (not shown) which constrain it to move only in a direction normal to the sample 5 surface. As the probe tip 15 approaches the sample surface to be tested, the stiffness S appears as a spring in parallel with the probe assembly mounting springs. Thus, the stiffness may be calculated by the computer using the above equation or could be displayed on a separate voltmeter (not shown) connected to the phase signal output of detector 35 and calibrated in accordance with the equation. It is seen that the value of S as the probe tip 15 approaches the sample will remain constant until contact with the sample surface is made. This sudden change in S may be used to indicate the point of contact with the surface.

In accordance with the present invention, the apparatus illustrated in FIG. 1 is used to characterize a scratch. A sample manipulation system, comprising the X-Y table 7 and the computer 19', permit the sample 5 to be accurately and precisely moved while the indenter is in contact with the surface. While this is done, the techniques described above with respect to determining stiffness are employed to measure the elastic stiffness of the contact as the sample 5 is moved laterally with respect to the indenter. The resulting plot shown in FIG. 2 indicates how the stiffness changed as the sample 5 moved. In the region "A" of the plot, the stiffness is not constant even though the force generated by the current in the coil 9 is held constant. The change in stiffness is in fact an indication of the change in the force between the indenter and the sample 5 resulting from the slight slope of the sample 5 relative to a plane perpendicular to the vertical motion of the indenter. In other words, the force between the indenter and the sample 5 changed as the point of contact between them moved in the vertical direction. This is due to the very low but finite stiffness springs used to hold the indenter column vertically. The important fact shown in FIG. 2 is that the elastic stiffness is very sensitive to this change and the change in the stiffness is indicating a real change in the contact area between the indenter and the sample 5 at very small loads and as the indenter is moving across the sample 5 surface.

Figure 2:
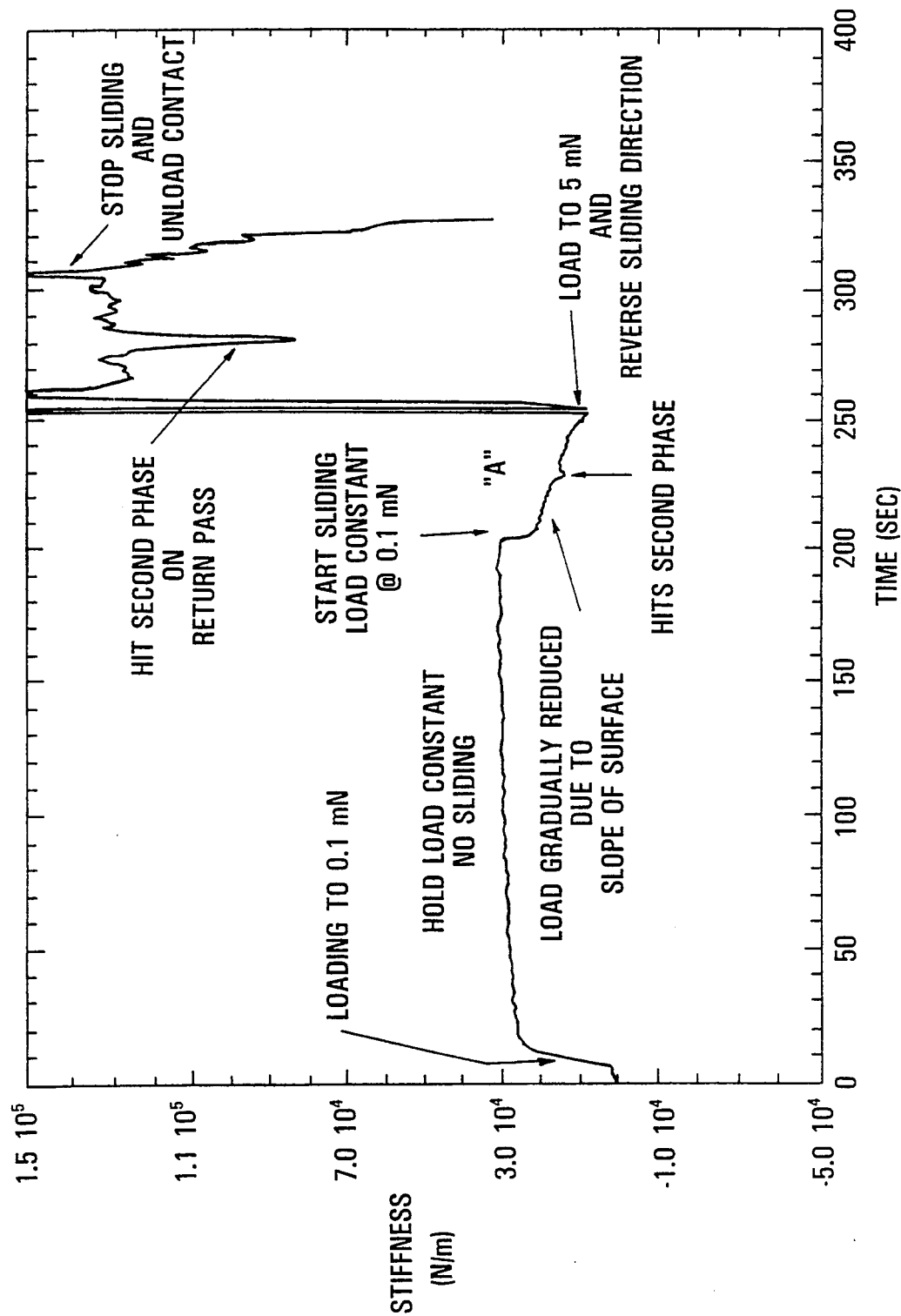
FIG. 2 is a graph showing the result obtained according to the present invention on a two phase material.

FIG. 2 is the result obtained according to the present invention on a two phase material. Initially, the load placed on the contact junction is set at 0.1 mN. The load is held constant without imparting sliding movement. After about 200 seconds, the sample 5 is moved to start sliding motion between the sample 5 and the indenter. Sliding proceeds while holding the load at 0.01 mN. In the region identified as "A" of the plot, the load gradually reduces due to the slope of the surface as described above. Also identifiable is a change in the stiffness due to the indenter passing over the second phase of the material.

After about 250 seconds, the load is increased to 5 mN and the sliding direction is reversed. Again, the second phase of the material is identified by a change in the stiffness. In the end, the sliding motion is ceased and the contact unloaded.

The aforementioned technique can be used to characterize a scratch while it is being produced during nanoscale machining processes, and can also be adapted for use in nanoprofilometry, atomic force microscopy images, very low load friction measurements, etc. Moreover, the technique allows the dimensions (contact area) to be measured during sliding contact to provide control information. Significantly, it is not necessary to know the interference or load on the contact to make the measurement.

Because of the precision measurements attained with the present invention, the techniques described herein can be used in the production of lithographic masks, micromachining, scratch hardness testing, and ultra sensitive profilometry.

While advantageous embodiments have been chosen to illustrate the invention, it will be understood by those skilled in the art that various changes and modifications can be made therein without departing from the scope of the invention as defined in the appended claims.

What is claimed is:

1. A method for continuously measuring scratch characteristics during sliding contact between first and second bodies, comprising the steps of:

applying an oscillating mechanical excitation at an arbitrary selected fixed frequency and a known amplitude to a contact junction of the first and second bodies and simultaneously applying a load independently of the fixed frequency to the contact junction;

measuring one of (a) the resulting mechanical response and (b) the resulting oscillatory displacement response between the first and second bodies relative to the applied oscillatory excitation at the load as an indication of the stiffness of contact between the first and second bodies;

imparting sliding contact between the first and second bodies by moving one relative to the other; and measuring changes in the measured stiffness over time while maintaining the load on the contact junction, the change in stiffness being indicative of scratch characteristics.

2. A method for continuously measuring scratch characteristics during sliding contact between first and second bodies, comprising the steps of:

determining contact stiffness between the first and second bodies at a predetermined load applied to a contact junction between the first and second bodies;

imparting sliding motion between the first and second bodies by moving one relative to the other; and measuring changes in the contact stiffness over time while maintaining the load on the contact junction, the change in stiffness being indicative of scratch characteristics.

3. A method according to claim 2, wherein the step of determining contact stiffness comprises applying an oscillating mechanical excitation at an arbitrary selected fixed frequency and a known amplitude to the contact junction of the first and second bodies and simultaneously applying a load independently of the fixed frequency to the contact junction; and measuring one of (a) the resulting mechanical response and (b) the resulting oscillatory displacement response between the first and second bodies relative to the applied oscillatory excitation at the load as an indication of the stiffness of contact between the first and second bodies.

* * * * *